United States Patent [19]

Thompson

[11] Patent Number: 4,706,662
[45] Date of Patent: Nov. 17, 1987

[54] FILM DRESSING WITH FABRIC BACKING

[75] Inventor: Darrell R. Thompson, Somerville, N.J.

[73] Assignee: Johnson & Johnson Products, Inc., New Brunswick, N.J.

[21] Appl. No.: 329,968

[22] Filed: Dec. 11, 1981

[51] Int. Cl.$^4$ ............................................. A61L 15/00
[52] U.S. Cl. .................................... 128/155; 128/156; 128/132 D
[58] Field of Search ................. 128/155, 156, 132 D; 604/389, 390; 428/40, 41, 261, 45, 46, 137

[56] References Cited

U.S. PATENT DOCUMENTS

| | | | |
|---|---|---|---|
| 3,490,971 | 1/1970 | Walters | 156/79 |
| 3,645,835 | 2/1972 | Hodgson | 128/156 |
| 3,698,395 | 10/1972 | Hasson | 128/155 |
| 3,774,592 | 11/1973 | Lahr | 128/2.1 E |
| 4,215,686 | 8/1980 | Gregory et al. | 128/156 |

Primary Examiner—C. Fred Rosenbaum
Assistant Examiner—Sherri E. Vinyard
Attorney, Agent, or Firm—Michael Q. Tatlow

[57] ABSTRACT

A dressing is disclosed which is made of a very thin film coated with an adhesive. In order to allow application of the dressing, the dressing has, on the surface opposite the adhesive, a fabric backing which is composed of a woven or non-woven fabric or a paper backing material. The dressing can be applied to the wound and the fibrous backing then removed, or the fibrous backing may be retained in place.

7 Claims, 3 Drawing Figures

FILM DRESSING WITH FABRIC BACKING

FIELD OF THE INVENTION

The present invention relates to surgical dressings made with a substrate of an extremely thin film and having a body-contacting adhesive on one surface of the film. The surgical dressings may be non-occlusive or occlusive.

PRIOR ART

Surgical dressings made with composite layers of film and adhesive which are non-occlusive, that is, which have high moisture vapor transmission rates, have been disclosed in U.S. Pat. Nos. 3,483,018 and 3,645,835. The moisture vapor transmission rate of these dressings is higher than the moisture vapor transmission rate of intact human skin. These dressings are made from films which may be transparent and which have moisture vapor transmission rates of greater than 10 grams per 100 square inches per 24 hours. These dressings are used in many applications and have an advantage in that they are impervious to bacteria and liquid water but allow oxygen to penetrate the dressing from the ambient atmosphere and allow moisture vapor from the skin of the patient to escape from beneath the dressing.

These dressings are made of continuous films, that is, films which are not perforated and are not microporous. The adhesive coating which is applied to these dressings also has a moisture vapor transmission rate which is sufficient to allow the composite dressing to have a moisture vapor transmission rate of at least 10 grams per 100 square inches per 24 hours.

In order to obtain the desired moisture vapor transmission rate, the dressings are made from extremely thin films of other polymeric materials, such as polyurethane, which have the desired moisture vapor transmission properties. These films are extremely thin, less than 10 mils, and are very flexible, limp and flimsy because of their thinness. These characteristics allow the dressing to be applied to the varying contours of the human body but also create significant problems in the application of the dressing to a patient. The thinness of the film and its flexibility and low weight very often cause the film to turn over onto itself during attempts to apply the film dressing to a patient. The film is similar in this property to polyvinylidene chloride film household wrap. When the adhesive surfaces of the film touch other adhesive surfaces on different portions of the film, the film dressing sticks to itself and makes it extremely difficult, if not impossible, to apply the dressing to the patient.

Occlusive film dressings, that is dressings which have very low moisture vapor transmission rates, i.e., below the rate of intact human skin, have also been used in some dressing applications. The dressings are employed to prevent moisture from escaping from the skin of the patient. The moisture vapor transmission rates of these dressings are less than 10 grams per 100 square inches for 24 hours. The occlusive film dressings are also made from extremely thin, usually transparent films and have the same difficulty in the application of the dressing to the patient as discussed above.

SUMMARY OF THE INVENTION

The present invention is directed to a film dressing which has significantly greater ease in the application of the dressing to a patient. The present dressing includes an easily removable, opaque, fibrous backing layer on that surface of the film which is opposite the adhesive surface that is applied to the skin of the patient. The fibrous backing layer may be a woven or non-woven fabric or a flexible paper sheet. Because of the weight and thickness of the fibrous backing layer relative to the film, the dressing has greatly improved handling properties and is very easy to apply to a patient. In the event that it is desirable to utilize the transparent characteristics of the film to examine a particular wound, the fibrous backing layer of the present invention can be easily removed from the dressing after the dressing is in place on the patient's skin, and the wound can be examined through the dressing without disturbing the dressing's position on the wound.

The dressings of the present invention have wide application in the treatment of wounds of all types. They may be used on surgical incissions, cuts and abrasions and as minor burn dressings.

DETAILED DESCRIPTION OF THE INVENTION

The invention will be better understood with reference to the following drawings in which.

Figure 1:
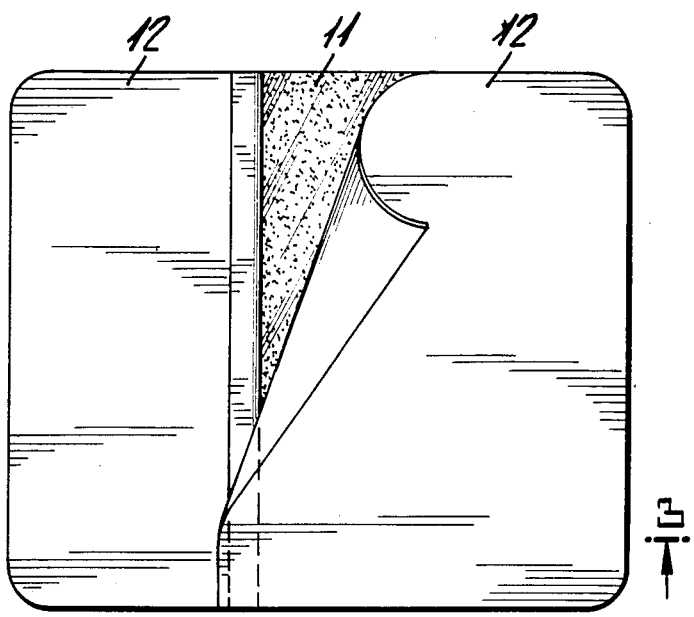
FIG. 1 is a bottom plan view of the dressing made in accordance with the present invention.
Figure 3:
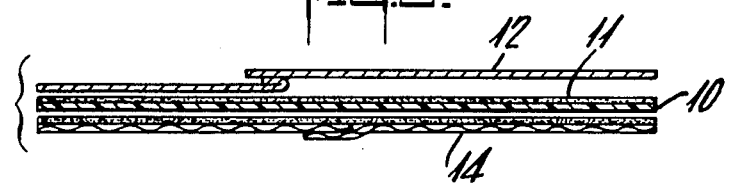
FIG. 3 is a cross-sectional view of the dressing made in accordance with the present invention taken along lines 2—2 in FIG. 1.
Figure 2:
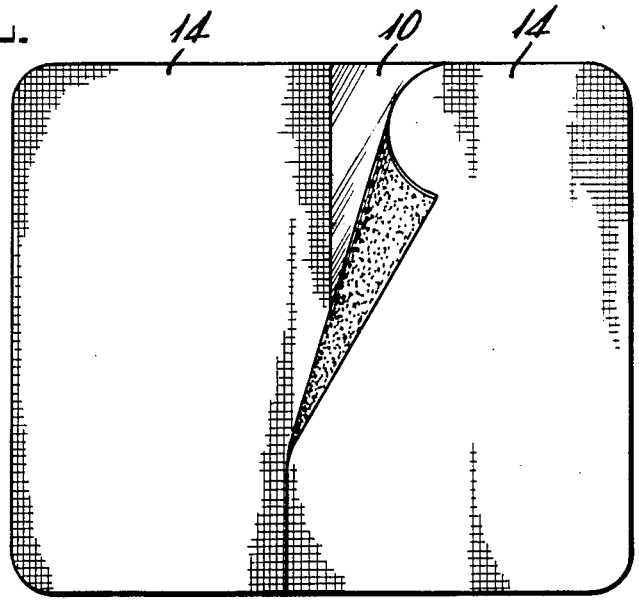
FIG. 2 is a top plan view of the dressing of the present invention.

The films that are useful in the present surgical dressings can be made from a large number of polymers. Suitable films can be made from: polyurethane; polyvinylchloride; polyvinylidene chloride; polyvinyl alcohol; polysulfone; polystyrene; polypropylene; polyethylene; polyamide; ethylene-vinylacetate copolymer; polyester; polycarbonate; ionomer; polyvinylfluoride and FEP fluoropolymer. The preferred moisture permeable film for a non-occlusive dressing is polyurethane, and the preferred moisture impermeable film for an occlusive dressing is polyvinylidine chloride.

The film used in the present dressing is made from synthetic polymers which are capable of being formed into continuous films by casting, extrusion or other known film-making processes. The film has a thickness less than 10 mils, usually of from 0.5 to 6 mils. The film is continuous, that is, it has no perforations or pores which extend through the depth of the film.

The non-occlusive high moisture vapor transmission films generally are hydrophilic, polymeric materials through which water vapor is capable of diffusing. Such films that may be used in the present invention include the polyurethane films which are described in U.S. Pat. No. 2,871,218 and the arylate copolymers which are described in U.S. Pat. No. 3,645,835. Generally, these films have moisture vapor transmission rates between about 10 and 80 grams per 100 square inches per 24 hours, as determined by ASTM Test E96 at 100° F. and 90% Relative Humidity. The preferred moisture vapor transmission rates are from 20 to 40 grams per 100 square inches for 24 hours.

The film is shown in the drawing as 10. On one surface of the film is a skin adhesive 11. The particular adhesive that is employed may be selected from one of the well-known skin contact adhesives such as those disclosed in U.S. Pat. Nos. 3,189,581; 3,268,357 and 3,325,459 and 4,112,213. The preferred adhesives are copolymers of 2-methylhexylacrylate and vinyl acetate in ratios of approximately 60 to 70 parts of the acrylate and 30 to 40 parts of the vinyl acetate. The polymers may also contain small amounts of N-tertiarybutyl acrylamide as a third monomer and a cross-linking agent. The preferred adhesive is a copolymer of approximately 70% 2-ethylhexylacrylate and 30% vinyl acetate and containing from 0.01 to 1% of a silane cross-linking agent as described in U.S. Pat. No. 4,112,213.

The adhesive is deposited on the film by solvent spreading, coating or extrusion. The level of the adhesive on the film should not be so great that the moisture vapor transmission characteristics of the film are impeded. Generally, a coating level of from 0.5 to 3 ounces per square yard is sufficient to obtain adequate skin adhesion but not so great as to interfere with the moisture vapor transmission characteristics desired in the finished dressing. The adhesive mass may be applied directly to the film or may be applied to a silicone-coated carrier sheet and the film applied to the adhesive on the carrier sheet. The adhesive-coated film may be removed from the carrier sheet) for subsequent processing, or the carrier sheet may remain with the film and become the release sheet 12 in the finished dressing.

As shown in the drawing on the side of the dressing opposite the release sheet 12, there is a fibrous backing, i.e., fabric or paper backing 14, covering on the upper surface of the dressing. This backing is adhered to the dressing by a layer of adhesive. The adhesive characteristics of the adhesive on the backing sheet are such that the backing sheet may be easily removed from the surface of the film to which it is applied. The backing may be any closely woven fabric, a knitted fabric, a nonwoven fabric or paper. The fibrous backing has a weight of from 1 to 3 ounces per square yard. The preferred fabric is a warp-knitted cellulose acetate fabric weighing approximately 2.3 ounces per square yard. Preferably, the backing fabric is applied to the film in two pieces in an overlapping fashion so that it may be readily removed from the film if desired. The backing may also be applied as a single piece of material with an edge free of adhesive to provide an adhesive free tab to remove the backing if desired. As shown in the drawings, the fibrous backing has the same outside dimensions as the film portion of the dressing. If the adhesive portion of the fibrous backing overlies the film portion of the dressing, there is a tendency to lift the film from the skin of the patient when the fibrous backing is removed. This is prevented by constructing the dressing so that the adhesive on the fibrous backing does not extend beyond the periphery of the film or by making the area of fibrous backing equal to or less than the area of the film. The presence of the fabric backing provides significant dimensional stability and ease of handling to the dressing. It also renders the otherwise transparent dressing opaque. In some instances, it is not desirable to have the wound visible to the patient or to others. The backing material being opaque prevents the wound from being seen, yet it can be readily lifted by a physician or nurse to examine the wound if desired. The adhesive on the fabric backing may be the same type of adhesive as employed as the skin contact adhesive but applied to the backing at lower coating levels, e.g., 0.5 to 5 ounces per square yard.

In general, the adherence of the fabric backing to the film is approximately half or less of the adherence of the film to the skin of the patient. That is, if the dressing itself requires a pull of 300 grams to remove the dressing from the skin, then the fabric backing would require 150 grams or less to remove the fabric backing from the film.

It should be recognized that the adhesive coating level on the fabric backing may be higher than the coating level on the film. Since the adhesive on the fabric backing penetrates the interstices of the backing, higher coating levels of adhesive may be necessary to give the desired degree of adherence of the fabric backing to the film. The dressings of the present invention may be constructed in many different dimensions. A dressing which is one inch by three inches may be used for minor incisions or cuts, while a dressing which is six inches by ten inches may be used as a burn dressing. A surgical dressing of the present invention was made in the following manner. A 2 mil thick polyurethane film was coated with an adhesive at a coating level of 2 ounces per square yard. The adhesive as a copolymer of approximately 70 parts 2-ethylhexylacrylate and approximately 30 parts of vinyl acetate and contained 0.01% of a silane cross-linking agent. A silicone release sheet was applied over the adhesive on the film. A tricot knitted fabric of cellulose acetate was coated with the same adhesive at a coating level of approximately 2.7 ounces per square yard. The knitted fabric was applied to the film on the side of the film opposite the release sheet. The completed dressing was readily handled and applied to human skin. The fabric backing could be readily removed without removing the film dressing from the skin.

I claim:

1. An adhesive dressing comprising a transparent continuous film of from 0.5 to 6 mils thick a skin-adhering adhesive applied to one surface of said film, a release sheet overlying the adhesive, an opaque, fibrous backing material removably secured to the side of the film opposite the release sheet to improve the handling characteristics of said dressing, said fibrous backing having the same outside dimensions as said film and being capable of being readily removed from said film without removing the film from the skin of a patient.

2. The adhesive dressing of claim 1 in which the film has a moisture vapor transmission rate of at least 20 and 40 grams per 100 square inches per 24 hours.

3. The adhesive dressing of claim 1 in which the film is polyurethane.

4. The adhesive dressing of claim 1 in which the fibrous backing is a warp knitted fabric.

5. The adhesive dressing of claim 1 in which the fibrous backing is adhesively secured to the film.

6. The adhesive dressing of claim 1 in which the force required to remove the fibrous backing from said film is less than one-half the force required to remove the film from the skin of a patient.

7. The adhesive dressing of claim 4 in which the fibrous backing is applied to the film in two pieces in an overlapping manner.

* * * * *